United States Patent
Liu et al.

(10) Patent No.: US 11,868,597 B2
(45) Date of Patent: Jan. 9, 2024

(54) METHOD AND APPARATUS FOR CONTROLLING DEVICES

(71) Applicant: HYTTO PTE. LTD., Singapore (SG)

(72) Inventors: Dan Liu, Guangdong (CN); Jilin Qiu, Guangdong (CN)

(73) Assignee: HYTTO PTE. LTD., Singapore (SG)

( * ) Notice: Subject to any disclaimer, the term of this patent is extended or adjusted under 35 U.S.C. 154(b) by 0 days.

(21) Appl. No.: 17/819,953

(22) Filed: Aug. 16, 2022

(65) Prior Publication Data

US 2023/0073832 A1    Mar. 9, 2023

Related U.S. Application Data

(63) Continuation-in-part of application No. 17/722,540, filed on Apr. 18, 2022, which is a continuation-in-part of application No. 17/671,783, filed on Feb. 15, 2022, and a continuation-in-part of application No. 17/088,476, filed on Nov. 3, 2020, now Pat. No. 11,503,384, said application No. 17/671,783 is a continuation-in-part of application No. 16/835,808, filed on Mar. 31, 2020, now Pat. No. 11,452,669, and a continuation-in-part of application No. 16/352,876, filed on Mar. 14, 2019, now Pat. No. 11,311,453.

(60) Provisional application No. 62/830,195, filed on Apr. 5, 2019.

(51) Int. Cl.
| | |
|---|---|
| *G06F 3/04845* | (2022.01) |
| *G06F 3/0488* | (2022.01) |
| *G06F 3/04847* | (2022.01) |
| *A61H 19/00* | (2006.01) |
| *G06F 3/0483* | (2013.01) |

(52) U.S. Cl.
CPC ........ *G06F 3/04845* (2013.01); *A61H 19/30* (2013.01); *A61H 19/40* (2013.01); *G06F 3/0488* (2013.01); *G06F 3/04847* (2013.01); *G06F 3/0483* (2013.01)

(58) Field of Classification Search
CPC ........ A61H 19/30; A61H 19/34; A61H 19/00; A61H 2201/5097; A61H 19/44; A61H 2201/1657; A61H 2201/5035; A61H 2201/5007; A61H 2201/5038; A61H 2201/5043; A61H 2201/5046; A61H 2201/5012; A61F 2005/417; A61F 5/41

See application file for complete search history.

(56) References Cited

U.S. PATENT DOCUMENTS 9,785,247 B1 * 10/2017 Horowitz ................ G06T 7/251
2020/0078260 A1 * 3/2020 Choudhury ............ A61H 19/34

* cited by examiner

*Primary Examiner* — Christine H Matthews
(74) *Attorney, Agent, or Firm* — Qinghong Xu

(57) ABSTRACT

A method for controlling devices includes: providing a first widget and a second widget on the user interface, wherein the first widget is associated with control of the first device, and the second widget is associated with control of the second device; activating joint control of the first device and the second device in response to a bundling operation used for bundling the first widget with the second widget; and driving, in response to an operation used for triggering the joint control, the first device and the second device to perform the respective predefined acts synchronously.

18 Claims, 11 Drawing Sheets

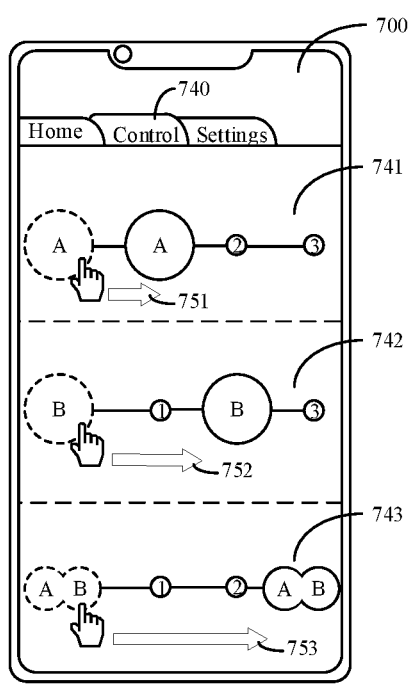 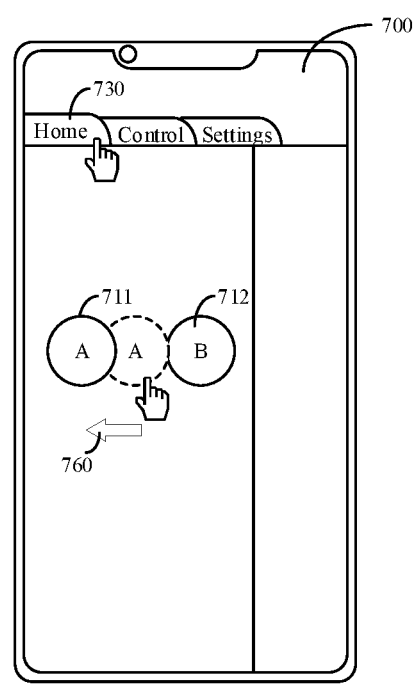
FIG. 7E
FIG. 7F

METHOD AND APPARATUS FOR CONTROLLING DEVICES

CROSS REFERENCE TO RELATED APPLICATION

This application is a continuation-in-part application of U.S. patent application Ser. No. 17/722,540 filed on Apr. 18, 2022, which is a continuation-in-part application of U.S. patent application Ser. No. 17/088,476 filed on Nov. 3, 2020 and Ser. No. 17/671,783 filed on Feb. 15, 2022, where the latter one is further a continuation-in-part application of U.S. patent application Ser. No. 16/352,876 filed on Mar. 14, 2019 and Ser. No. 16/835,808 filed on Mar. 31, 2020, where the latter one further claims the benefit of U.S. Provisional Application No. 62/830,195, filed on Apr. 5, 2019, all of which are hereby incorporated by reference in their entireties.

TECHNICAL FIELD

The disclosure relates to the field of adult toy, and in particular, to a method, an apparatus and a non-transitory storage medium for controlling devices.

BACKGROUND

Conventional control of adult toys typically involves direct control of these devices by a user or through an operation of a user device such as a phone or a tablet of the user. However, conventional systems are only capable of controlling different adult toys independently of each other.

Accordingly, a need in the art exists for an efficient technique for controlling multiple different adult toys or multiple different parts of one or more adult toys in a joint manner.

It should be noted that, information disclosed in the above background portion is provided only for better understanding of the background of the disclosure, and thus it may contain information that does not form the prior art known by those ordinary skilled in the art.

SUMMARY

The disclosure provides a method, an apparatus and a non-transitory storage medium for controlling devices.

According to some embodiments of the disclosure, there is provided a method for controlling devices implemented by a user terminal, where the user terminal includes a user interface and is in communication with a first device and a second device, the first device and the second device are configured to perform respective predefined acts sexually stimulating one or more human users, and the method includes:
  providing a first widget and a second widget on the user interface, where the first widget is associated with control of the first device, and the second widget is associated with control of the second device;
  activating joint control of the first device and the second device in response to a bundling operation used for bundling the first widget with the second widget; and
  driving, in response to an operation used for triggering the joint control, the first device and the second device to perform the respective predefined acts synchronously.

According to some embodiments of the disclosure, there is provided a user terminal, including:
  a touch screen, configured to display a user interface;
  a communication interface, configured to communicate with a first device and a second device, where the first device and the second device are configured to perform respective predefined acts sexually stimulating one or more human users;
  a memory, configured to store instructions; and
  a processor, where the processor is, through executing the instructions, configured to: provide, through the touch screen, a first widget and a second widget on the user interface, where the first widget is associated with control of the first device, and the second widget is associated with control of the second device; activate joint control of the first device and the second device in response to a bundling operation used for bundling the first widget with the second widget; and drive, in response to an operation used for triggering the joint control, the first device and the second device to perform the respective predefined acts synchronously.

According to some embodiments of the disclosure, there is provided a non-transitory computer-readable storage medium storing computer-executable instructions, where the computer-executable instructions are used for, when being executed by a processor of a user terminal, implementing a method for controlling devices,
  where the user terminal includes a user interface and is in communication with a first device and a second device, the first device and the second device are configured to perform respective predefined acts sexually stimulating one or more human users, and
  the method includes: providing a first widget and a second widget on the user interface, where the first widget is associated with control of the first device, and the second widget is associated with control of the second device; activating joint control of the first device and the second device in response to a bundling operation used for bundling the first widget with the second widget; and driving, in response to an operation used for triggering the joint control, the first device and the second device to perform the respective predefined acts synchronously.

It is to be understood that both the foregoing general description and the following detailed description are exemplary and explanatory only and are not restrictive of the invention, as claimed.

This section provides a summary of various implementations or examples of the technology described in the disclosure, and is not a comprehensive disclosure of the full scope or all features of the disclosed technology.

BRIEF DESCRIPTION OF THE DRAWINGS

In order to more clearly illustrate the technical solutions of the embodiments of the disclosure, drawings of the embodiments of the disclosure will be briefly described below. It will be apparent that the drawings in the following description refer only to some embodiments of the disclosure, and are not intended to limit the disclosure.

FIG. 7A to FIG. 7F illustrate an exemplary user interface 700 provided by the user terminal 105;

DETAILED DESCRIPTION

Figure 1:
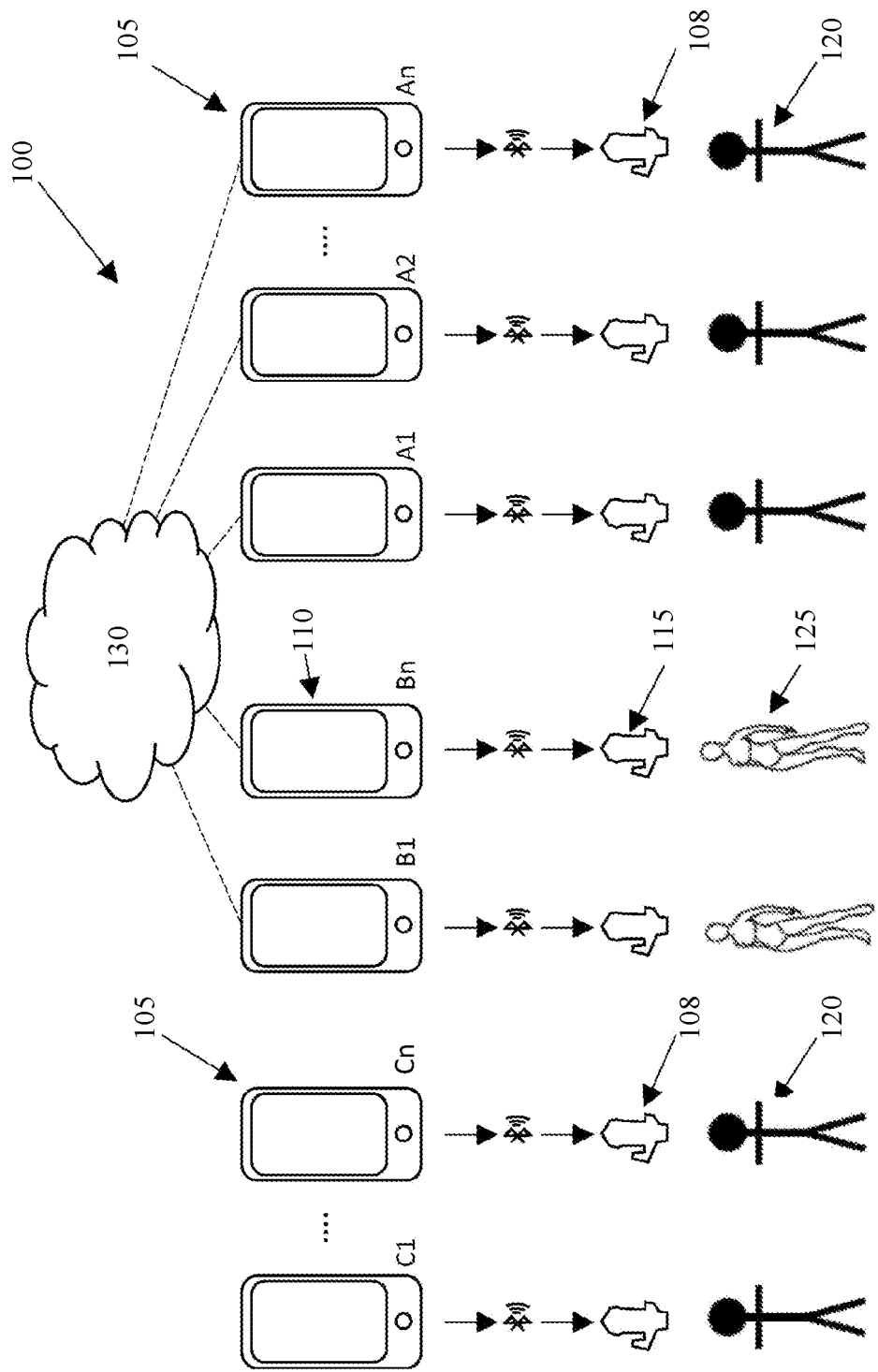
FIG. 1 illustrates an exemplary system 100 for controlling devices.

Hereinafter, the method, apparatus and non-transitory storage medium for controlling devices according to the disclosure will be described in further detail with reference to the accompanying drawings and particular embodiments of the disclosure, such that those skilled in the art may have a better understanding of technical solutions of the disclosure.

In order to make the objectives, technical solutions and advantages of some embodiments of the disclosure clearer, the technical solutions of some embodiments of the disclosure will be described clearly and completely in conjunction with the accompanying drawings of the embodiments of the disclosure. It is obvious that the described embodiments are part of the embodiments rather than all embodiments of the disclosure. All other embodiments obtained by one of ordinary skill in the art based on the described embodiments of the disclosure without the need for creative work are within the scope of the disclosure.

In the description of the embodiments of the disclosure, it is to be noted that the directional or positional relationships indicated by the terms "upper", "lower", "top", "bottom" or the like are based on the directional or positional relationships shown in the drawings, which are provided only for the purpose of facilitating the description and simplification of the description and is not intended or implied that the device or element referred to must have a specific orientation, constructed or operated in a particular orientation. Accordingly, it should not be construed as a limitation of this disclosure.

FIG. 1 illustrates an exemplary system 100 for controlling devices. In at least some exemplary embodiments, system 100 may be a system for controlling devices synchronously in real-time (e.g., in real-time or in near real-time) for an adult entertainment application. The exemplary disclosed system, apparatus, and method may be an online adult entertainment system, apparatus, and method. The exemplary disclosed system, apparatus, and method may be a telecommunications system, apparatus, and method for adult entertainment.

As illustrated in FIG. 1, system 100 may include one or more user terminals 105, one or more model devices 110, one or more user accessories 108, and one or more model accessories 115. For example, system 100 may include a plurality of user terminals 105, a plurality of user accessories 108, a plurality of model devices 110, and a plurality of model accessories 115. Data such as image data, audio data, and/or control data may be transferred between user terminals 105, user accessories 108, model devices 110, and model accessories 115.

As illustrated in FIG. 1, system 100 may include any desired number of user terminals 105 (e.g., A1, A2, . . . An). User terminal 105 may be any suitable device for interfacing with other components of system 100 such as the exemplary disclosed accessories and/or other computing devices (e.g., user interface). For example, user terminal 105 may be any suitable user interface for receiving input and/or providing output (e.g., image data) to a user 120. User terminal 105 may include a camera and a microphone. User terminal 105 may be, for example, a touchscreen device (e.g., of a smartphone, a tablet, a smartboard, and/or any suitable computer device), a wearable device, a computer keyboard and monitor (e.g., desktop or laptop), an audio-based device for entering input and/or receiving output via sound, a tactile-based device for entering input and receiving output based on touch or feel, a dedicated user interface designed to work specifically with other components of system 100, and/or any other suitable user interface. For example, user terminal 105 may include a touchscreen device of a smartphone or handheld tablet. For example, user terminal 105 may include a display (e.g., a computing device display, a touchscreen display, and/or any other suitable type of display) that may provide output, image data, and/or any other desired output or input prompt to a user. For example, the exemplary display may include a graphical user interface to facilitate entry of input by a user and/or receiving output such as image data. An application for example as described herein and/or a web browser may be installed on user terminal 105 and utilized by user 120. Model device 110 may be similar to user terminal 105.

Figure 2:
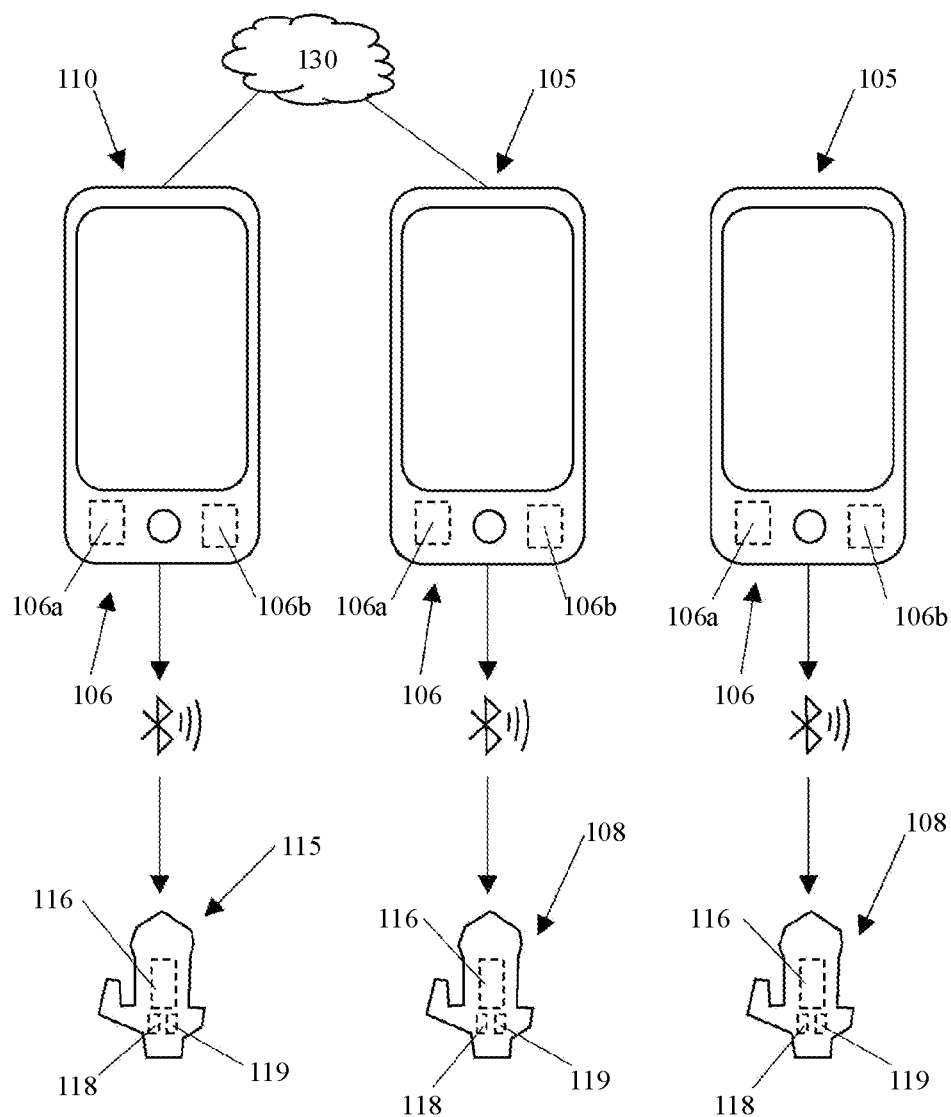
FIG. 2 illustrates an exemplary user terminal 105.

As illustrated in FIG. 2, user terminal 105 may include a sensor array 106. In at least some exemplary embodiments, sensor array 106 may include one or more sensors integrated or built into the exemplary disclosed user terminal (e.g., user terminal 105) such as, for example, a mobile phone, a pad, or a wearable device. Sensor array 106 may also include an audio sensor (e.g., a microphone) for sensing, detecting, and recording ambient or nearby noise or sound. For example, sensor array 106 may operate to detect and/or record noise or sound at a location of user terminal 105. Sensor array 106 may include any suitable sensors for use with system 100 such as, for example, a location sensor 106a and a movement sensor 106b. Location sensor 106a may include a GPS device, a Galileo device, a GLONASS device, an IRNSS device, a BeiDou device, and/or any other suitable device that may operate with a global navigation system.

Movement sensor 106b may include any suitable components for sensing motion (e.g., motion amplitude), velocity, and/or acceleration. Movement sensor 106b may include an acceleration sensor. Movement sensor 106b may include a gyroscope. For example, movement sensor 106b may include a displacement sensor, a velocity sensor, and/or an accelerometer. For example, movement sensor 106b may include components such as a servo accelerometer, a piezoelectric accelerometer, a potentiometric accelerometer, and/or a strain gauge accelerometer. Movement sensor 106b may include a piezoelectric velocity sensor or any other suitable type of velocity or acceleration sensor.

System 100 may include any desired number of model devices 110 (e.g., B1 . . . Bn). Model device 110 may be similar to user terminal 105. For example, model device 110 may include any suitable user interface for receiving input and/or providing output (e.g., image data) for a model 125. Model 125 may operate model device 110 to record and transfer image (e.g., video) and audio data to one or more users 120 via a network 130. One or more models 125 may use respective model devices 110 to communicate with one or more users 120 using respective user terminals 105 via network 130 or directly.

Model accessory 115 may be any suitable accessory for use by model 125 (e.g., when model 125 is imaged by model device 110). For example, model accessory 115 may be a prop that is used by model 125 while model 125 is being imaged (e.g., a video or pictures of model 125 are being recorded and/or transmitted for example via model device 110 synchronously in real-time to be viewed by user 120). For example, model accessory 115 may be a device used for erotic stimulation (e.g., a sex aid or a "sex toy"). Model accessory 115 may be a sexual simulation device that may be associated with a given model 125 and respective model device 110 of that given model 125. In at least some exemplary embodiments, model accessory 115 may be a massaging apparatus for human genitalia (e.g., a vibrator). For example, model accessory 115 may be any suitable device for use in a video or pictures recorded by model device 110, which may be an erotic video or erotic pictures). In at least some exemplary embodiments, model accessory 115 may be a tool or other indicator that may be used in video or pictures recorded by model device 110 such as surveying equipment, a sign providing information such as location or time information, a surveillance tool used by model 125, and/or any other suitable tool or accessory that may be used while model device 110 is recording a video or pictures of model 125. For example, model 125 may be an erotic model using model accessory 115 that may be an erotic device, a technician or laborer using model accessory 115 that may be a tool or work device specific to a desired application, an operative using model accessory 115 that may be a surveillance tool or a part of a weapon system being recorded by model device 110, and/or any other desired role using any suitable model accessory 115.

Model accessory 115 may include a motor 116. Motor 116 may include an electric motor. Motor 116 may include a server motor, a stepper motor, a brushless motor, or any other suitable type of motor. Motor 116 may include any suitable vibration motor or haptic motor such as, for example, a mini vibrator motor. Motor 116 may include a low voltage motor. Motor 116 may include a pager motor or a coin vibration motor. Motor 116 may include a linear resonant actuator or an eccentric rotating mass vibration motor. Motor 116 may be powered by any suitable power source, such as a battery (e.g., a nickel-metal hydride battery, a lithium-ion battery, an ultracapacitor battery, a lead-acid battery, and/or a nickel cadmium battery), an electric power source (e.g., a transformer connected to a plug that may plug into an outlet), and/or any other suitable energy source. Model accessory 115 may include a controller 119 that may be any suitable computing device for controlling an operation of motor 116 and a communication device 118. Controller 119 may, for example, include components similar to the components described below regarding FIG. 11. Controller 119 may include for example a processor (e.g., micro-processing logic control device) or board components. Controller 119 may control motor 116 based on input data and/or commands received from user terminal 105 and/or model device 110 via network 130 and/or a communication device 118 (e.g., transferred directly to communication device 118 by any suitable component of system 100). Motor 116 may be controlled by controller 119 to vibrate model accessory 115 at a desired level or strength, perform a suction operation at a desired level or strength using model accessory 115 (e.g., using model accessory 115 as a suction device), rotate or swing model accessory 115 at a desired speed or amount, contract or expand model accessory 115 by a desired amount, cause model accessory 115 to perform an inhalation action, and/or cause model accessory 115 to perform any other suitable action or function.

In at least some exemplary embodiments, motor 116 may be or may include a thermal device such as a heater. In at least some exemplary embodiments, motor 116 may include an electric heating device such as an electric resistance heating device or any other suitable heating or cooling device. Motor 116 may include a polyimide heater, a silicone rubber heater, and/or a resistive wire heater. Motor 116 may be controlled by controller 119 to heat or emit heat or warmth from model accessory 115. For example, motor 116 may cause a temperature variation of model accessory 115.

User accessory 108 may be similar to model accessory 115. User accessory 108 may be a sexual simulation device that may be associated with a given user 120 (e.g., a viewer of one or more models 125) and respective user terminal 105 (e.g., a viewer device) of that given user 120. A given user 120 may operate a given user accessory 108 similarly to as described above regarding an operation of a given model accessory 115 by a given model 125.

Network 130 may be any suitable communication network over which data may be transferred between one or more user terminals 105, one or more user accessories 108, one or more model devices 110, and/or one or more model accessories 115. Network 130 may be the internet, a LAN (e.g., via Ethernet LAN), a WAN, a WiFi network, or any other suitable network. The components of system 100 may also be directly connected (e.g., by wire, cable, USB connection, and/or any other suitable electro-mechanical connection) to each other and/or connected via network 130. For example, components of system 100 may wirelessly transmit data by any suitable technique such as, e.g., wirelessly transmitting data via 4G LTE networks (e.g., or 5G networks) or any other suitable data transmission technique for example via network communication. User terminals 105, user accessories 108, model devices 110, and/or model accessories 115 may include any suitable communication components for communicating with other components of system 100 using for example the communication techniques described above. For example, user terminals 105 and model devices 110 may include integrally formed communication devices (e.g., smartphone components), and user accessories 108 and model accessories 115 may each include communication device 118 that may communicate using any of the exemplary disclosed communication techniques.

In at least some exemplary embodiments, a given model accessory 115 may communicate with a given model device 110 (e.g., a paired model device 110) via any suitable short distance communication technique. For example, model accessories 115 (e.g., via communication device 118) and model devices 110 may communicate via WiFi, Bluetooth, ZigBee, NFC, IrDA, and/or any other suitable short distance technique. Model accessory 115 may be an adult toy that may be connected with model device 110 through short distance wireless communication. An application (e.g., operating using the exemplary disclosed modules) may be installed on model device 110, the application and model device 110 being configured to send commands to model accessory 115 to drive (e.g., actuate) model accessory 115. User accessory 108 may communicate with user terminal 105 similarly to the communication of model accessory 115 and model device 110 described above.

In at least some exemplary embodiments, user accessory 108 may operate with and communicate with user terminal 105, and model accessory 115 may operate with and communicate directly with model device 110, independently of network 130. For example, as illustrated in FIG. 1, any desired number of user terminals 105 (e.g., Cl Cn) may be in an offline mode that may be disconnected from network 130 while communicating with respective user accessories 108. Model devices 110 and model accessories 115 may similarly operate in an offline mode.

System 100 may include one or modules for performing the exemplary disclosed operations. The one or more modules may include an accessory control module for controlling user accessory 108 and model accessory 115. The one or more modules may be stored and operated by any suitable components of system 100 (e.g., including processor components) such as, for example, network 130, user terminal 105, user accessory 108, model device 110, model accessory 115, and/or any other suitable component of system 100. For example, system 100 may include one or more modules having computer-executable code stored in non-volatile memory. System 100 may also include one or more storages (e.g., buffer storages) that may include components similar to the exemplary disclosed computing device and network components described below regarding FIGS. 11 and 12. For example, the exemplary disclosed buffer storage may include components similar to the exemplary storage medium and RAM described below regarding FIG. 11. The exemplary disclosed buffer storage may be implemented in software and/or a fixed memory location in hardware of system 100. The exemplary disclosed buffer storage (e.g., a data buffer) may store data temporarily during an operation of system 100.

Figure 3:
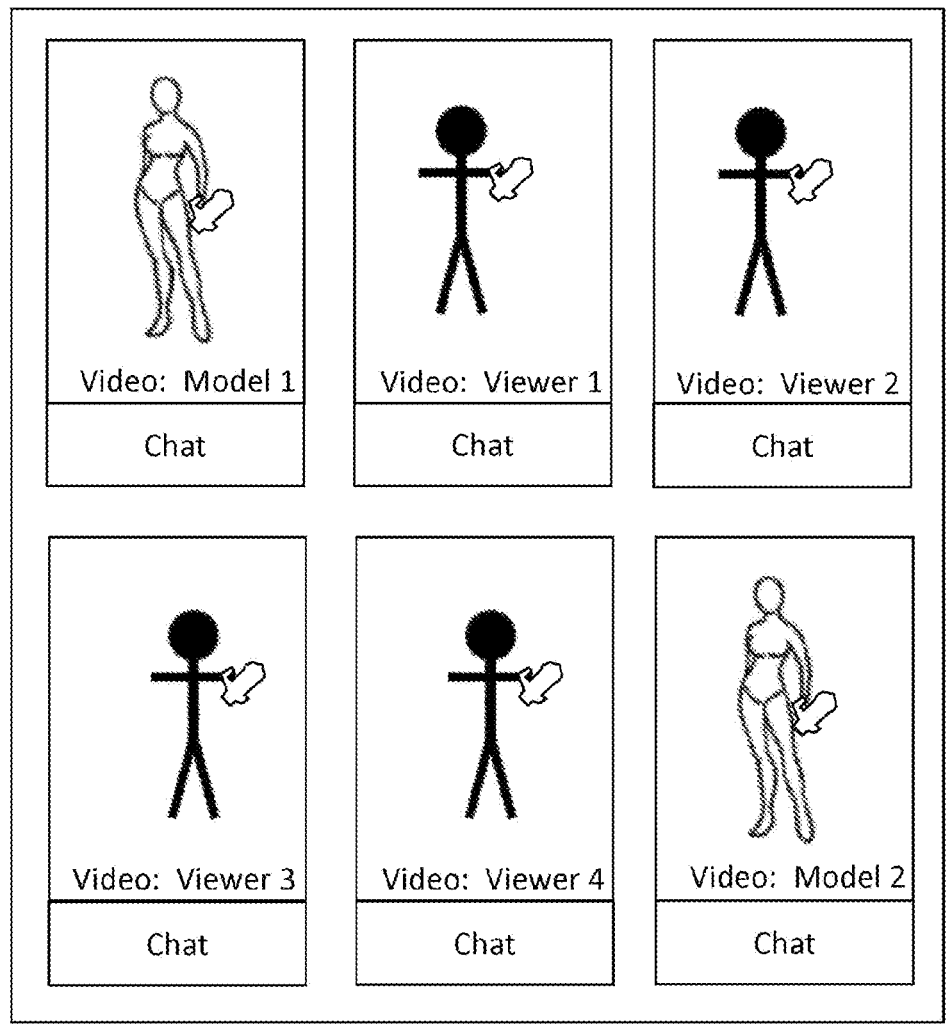
FIG. 3 illustrates an exemplary implementation scenario.

The one or more exemplary disclosed modules may also provide a chat room interface via user terminal 105 and model device 110 for use by each user 120 and model 125. For example, video display of model 125, one or more users 120, and/or and a chat or messaging app (e.g., any suitable chat communication or messaging app such as, for example, text, voice, and/or video chat boxes) may be displayed to each user 120 via user terminal 105 and to each model 125 via model device 110. One or more users 120 and one or more models 125 may thereby view and chat (e.g., text, voice, and/or video chat) with each other via the one or more exemplary disclosed modules via respective user terminals 105 and model devices 110. Each user 120 may thereby view, interact with, and/or chat (e.g., text, voice, and/or video chat) with one or more models 125 and/or other users 120. Also, each model 125 may thereby view, interact with, and/or chat with one or users 120 and/or other models 125. For example, multiple text, voice, and/or video chat boxes including a plurality of users 120 (e.g., viewers each having one or more user accessories 108) and/or a plurality of models 125 (e.g., each having one or more model accessories 115) may be displayed to each user 120 and each model 125 via respective user terminals 305 and model devices 110. Users 120 and models 125 may thereby view and interact with other users 120 and models 125 that may each have one or more respective accessories (e.g., respective user accessories 108 and model accessories 115). FIG. 3 schematically illustrates an exemplary embodiment of the exemplary disclosed chat room that may be displayed to user 120 via user terminal 105 or to model 125 via model device 110.

The exemplary disclosed system, apparatus, and method may be used in any suitable application for controlling devices. For example, the exemplary disclosed system, apparatus, and method may be used in any suitable application for controlling devices. The exemplary disclosed system, apparatus, and method may be used in any suitable application for controlling adult toys or different parts of one adult toy or different parts of different adult toys.

More details of the system 100 may refer to U.S. applications No. 17,671,783 and No. 17,722,540, the content of which is incorporated here in entirety by reference.

Figure 4:
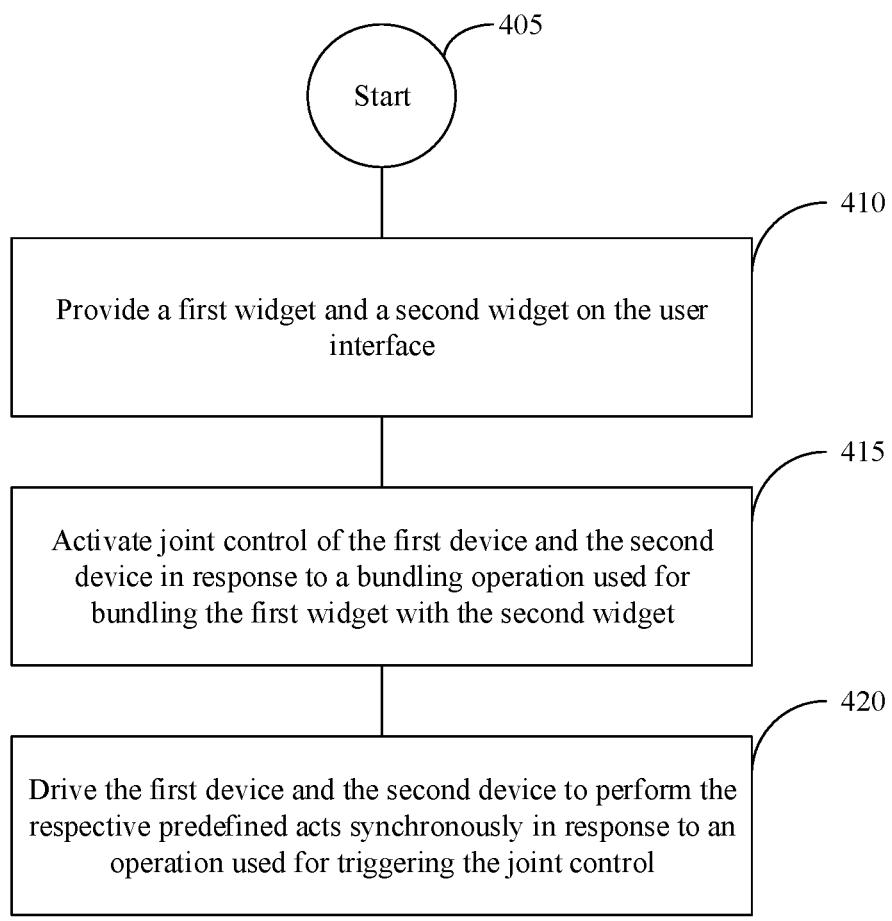
FIG. 4 illustrates an exemplary process 400 according to some embodiments.

An exemplary operation of the exemplary disclosed method and user terminal will now be described. FIG. 4 illustrates an exemplary process 400 of user terminal 105. The user terminal 105 provides a user interface and is in communication with a first device and a second device, the first device and the second device are configured to perform respective predefined acts sexually stimulating one or more human users.

In some embodiments, the first device is a first adult toy, and the second device is a second adult toy.

In some embodiments, the first device is a part of the first adult toy, and the second device is a part of the second adult toy.

In some embodiments, the first device is a part of the first adult toy, and the second device is another part of the first adult toy.

It should be noted that the first device and second device are only exemplary herein, rather than limiting scope of the disclosure. In some embodiments, the number of devices is not limited to two, but may be three and more. For example, the user terminal 105 is further in communication with devices other than the first and second devices.

In some embodiments, the predefined act to be performed by any one of the first and second devices includes vibration, rotation, suction, expansion, contraction, bending, temperature control, stretching, reciprocation, and combinations thereof, but is not limited thereto.

In some embodiments, the communication between the user terminal 105 and any one of the first and second devices is implemented in any suitable manner. For example, the communication may be implemented in the manner of short-range communication, such as WiFi, Bluetooth, Infrared or radio wave. For another example, the communication may be implemented in the manner of long-range communication, such as Internet, cellular network or control link. Herein, an exemplary scenario of cellular network includes communication via application programs installed on different cellular phones; and an exemplary scenario of control link includes communication established among multiple mobile terminals in such a manner, that a human user(s) of a mobile terminal(s) can be sexually stimulated by or sexually stimulates another human user(s) of another mobile terminal(s).

Further referring to FIG. 4, the process 400 begins at step 405.

At step 410, the user terminal 105 provides a first widget and a second widget on the user interface, where the first widget is associated with control of the first device, and the second widget is associated with control of the second device.

After establishing respective communication connections with the first device and the second device, the user terminal 105 provides the first widget and the second widget respectively associated with the control thereof. The first and second widgets may be displayed in a manner corresponding to the first and second devices, respectively, such that a human user is illustratively indicated to operates on the first widget when he/she intends to drive the first device, and operates on the second widget when he/she intends to drive the second device. For example, the first widget is displayed on the user interface with an icon corresponding to the first device, and the second widget is displayed on the user interface with another icon corresponding to the second device.

The first and second widget are respectively associated with the control of the first and second device. For example, upon receiving an operation with respect to the first widget, the user terminal 105 generates a corresponding signal (set) conforming to a protocol predefined by a manufacturer of the first device, and then transmits the signal (set) to the first device via the communication connection established between the user terminal 105 and the first device, thereby driving the first device to perform a predefined act corresponding to the operation received by the user terminal 105. Similarly, upon receiving an operation with respect to the second widget, the user terminal 105 generates a signal (set) that is readable and executable by the second device, and then transmits the signal (set) to the second device via the communication connection established between the user terminal 105 and the second device, thereby driving the second device to perform a predefined act corresponding to the operation received by the user terminal 105.

In some embodiments, the first widget and the second widget may be displayed on the user interface in any suitable manner as long as the display manner thereof is able to clearly represent to the human user the association between each widget and the control of its corresponding device. Exemplary details with respect to the display manner of the first and second widgets may refer to FIG. 7A and FIG. 9A.

As described above, the number of devices is not limited to two, but may be three and more. Accordingly, the user terminal 105 may provide additional widgets associated with control of the other devices.

At step 415, the user terminal 105 activates joint control of the first device and the second device in response to a bundling operation used for bundling the first widget with the second widget.

In some embodiments, step 415 is performed by providing, in response to an operation used for bundling the first widget with the second widget, a visual bundling indicator on the user interface, where the visual bundling indicator indicates joint control of the first device and the second device.

The operation used for bundling the first widget with the second widget is also referred to as a bundling operation hereafter. The visual bundling indicator used for indicating joint control of the first device and the second device is also referred to as a bundling indicator hereafter.

In some embodiments, the bundling operation includes a touch control operation performed on at least one of the first widget and the second widget.

In some embodiments, the bundling operation includes a dragging operation. For example, the user terminal 105 detects a dragging operation with respect to the first widget, further detects that an icon corresponding to the first widget is dragged toward and close to an icon corresponding to the second widget within a preset range and, accordingly, determines the dragging operation as a bundling operation. Details of the dragging operation may further refer to the description of FIG. 6 below.

In some embodiments, the bundling operation includes a check-box operation. For example, the user terminal 105 detects a selection operation on a check box of the first widget and highlights the icon corresponding to the first widget; then detects another selection operation on a check box of the second widget and highlights the icon corresponding to the second widget; and highlighting of both the first widget and the second widget indicates the joint control of the first device and the second device. Details of the check-box operation may further refer to the description of FIG. 8 below.

In some embodiments, the bundling operation is able to be implemented in any suitable manner. For example, in addition to the dragging operation and check-box operation described above, the bundling operation may further include selecting both the first and second widgets with a circle or frame, dragging the first and second widgets into a predefined area on the user interface, or confirming a recommendation proposed by the user terminal autonomously (e.g., through artificial algorithm based on user profile).

In some embodiments, the bundling indicator varies depending on the implementation manner of the bundling operation. For example, when the bundling operation is implemented through the dragging operation as described above, the bundling indicator may include an icon, which is different from any one of the first and second widgets. For another example, when the bundling operation is implemented through the check-box operation as described above, the bundling indicator may include the highlighting of both the first and second widgets. In other words, the bundling indicator may be displayed on the user interface in any suitable manner as long as the display manner thereof is able to clearly represent to the human user the association between it and the joint control of the first and second devices. Exemplary details with respect to the display manner of bundling indicator may refer to FIGS. 6 and 8.

Moreover, step 415 is described above as providing the visual bundling indicator, but the disclosure is not limited thereto. In some embodiments, the bundling of the first widget and the second widget is implementable at the system background of the user terminal 105 without displaying any visual indicator or providing any other indication.

In some other embodiments, a human user of the user terminal 105 may be informed of the activation of the joint control, that is, the bundling between the first device/widget and the second device/widget through other functional elements of the user terminal 105, for example, a vibrator, a speaker, a flash, or the like. For example, after receiving a bundling operation on the user interface, the user terminal 105 may inform the human user of the bundling by playing a preset voice message, so as to indicate activation of the joint control of the first device and the second device. Any combination of these informing manners, including the visual indicator, is also available, and details thereof will be omitted here for brevity.

At step 420, the user terminal 105 drives, in response to an operation used for triggering the joint control, the first device and the second device to perform the respective predefined acts synchronously.

The operation used for triggering the joint control of the first and second devices is also referred to as a joint-control operation hereafter.

In some embodiments, after receiving the bundling operation, the user terminal 105 binds the control of first and second devices together. In other words, instead of or in addition to drive the first and second devices through the first and second widgets, respectively, the user terminal 105 is able to generate a control signal set, including control signals with respect to the first and second devices, in response to a single operation, that is, the joint-control operation. Accordingly, the user terminal 105 may send the control signals to the first and second devices at the same time, respectively, through the communication connection between the user terminal 105 and the first device and through the communication connection between the user terminal 105 and the second device.

The joint-control operation may be implemented in any suitable manner. In some embodiments, an implementation manner of the joint-control operation varies depending on the display manner of the bundling indicator. For example, when the bundling indicator includes an icon generated in response to the dragging bundling operation, the joint-control operation may be performed with respect to the generated icon. For another example, when the bundling indicator includes highlighting of the first and second widgets in response to the check-box bundling operation, the joint-control operation may be performed with respect to a control panel independent of the first and second widget. Exemplary details with respect to the implementation manner of joint-control operation may refer to FIGS. 6 and 8.

In some embodiments, the joint-control operation is also implementable through any proper manner including, but not limited to, a touch operation, a mouse/key input, a gesture input, a voice instruction, a decibel control operation, a music control operation, a pose change of the user terminal, a remote control from another user, or distance sensing. The touch operation is taken as an example for describing the joint-control operation in this disclosure, but should not be construed as a limitation thereto.

In some embodiments, upon receiving the joint-control operation, the user terminal 105 generates the control signal set as described above and, then, send the control signals therein to the first and second devices at the same time, so as to drive the first device and the second device to perform the respective predefined acts in a synchronous manner. Specifically, upon receiving the control signal (set) transmitted via the communication connection between the user terminal 105 and the first device, the first device is driven to perform a first act or a set of first acts. Similarly, upon receiving the control signal (set) transmitted via the communication connection between the user terminal 105 and the second device, the second device is driven to perform a second act or a set of second acts.

In some embodiments, the synchronous manner includes performing the respective predefined acts at the same time, or at the same level, or in the same pattern, or any combination of above.

In some embodiments, performing the respective predefined acts at the same time includes that the first and second devices are driven in such a way that the predefined act of the first device and the predefined act of the second device start at the same time and/or stop at the same time.

In some embodiments, performing the respective predefined acts at the same level includes that the first and second devices are driven in such a way that the predefined act of the first device and the predefined act of the second device are performed at a same level of amplitude, frequency, speed, acceleration, temperature, and any combinations thereof.

In some embodiments, performing the respective predefined acts at the same pattern includes that the first and second devices are driven in such a way that the predefined act of the first device and the predefined act of the second device are performed cooperatively with a same profile. For example, a set of first acts corresponding to the first device and a set of second acts corresponding to the second device are recorded previously as a pattern profile or separate patterns that are played simultaneously. Upon receiving a joint-control operation for triggering playback of the pattern profile, the set of first acts and the set of second acts are to be performed by the first device and the second device respectively and cooperatively. Taking two vibrators as an example of the first and second devices, upon receiving the joint-control operation for triggering playback of the pattern profile, the vibrators may be driven to vibrate at an identical interval or at alternative intervals.

According to at least some embodiments of the disclosure, multiple devices communicated with the user terminal can be driven to perform respective predefined acts synchronously in response to the bundling operation as received. In this way, user experience brought about by different adult toys can be greatly improved through intuitive and concise user interface, without necessity to design complex interfaces for these toys or learn complex operations caused by frequent switching between different interfaces.

Figure 5:
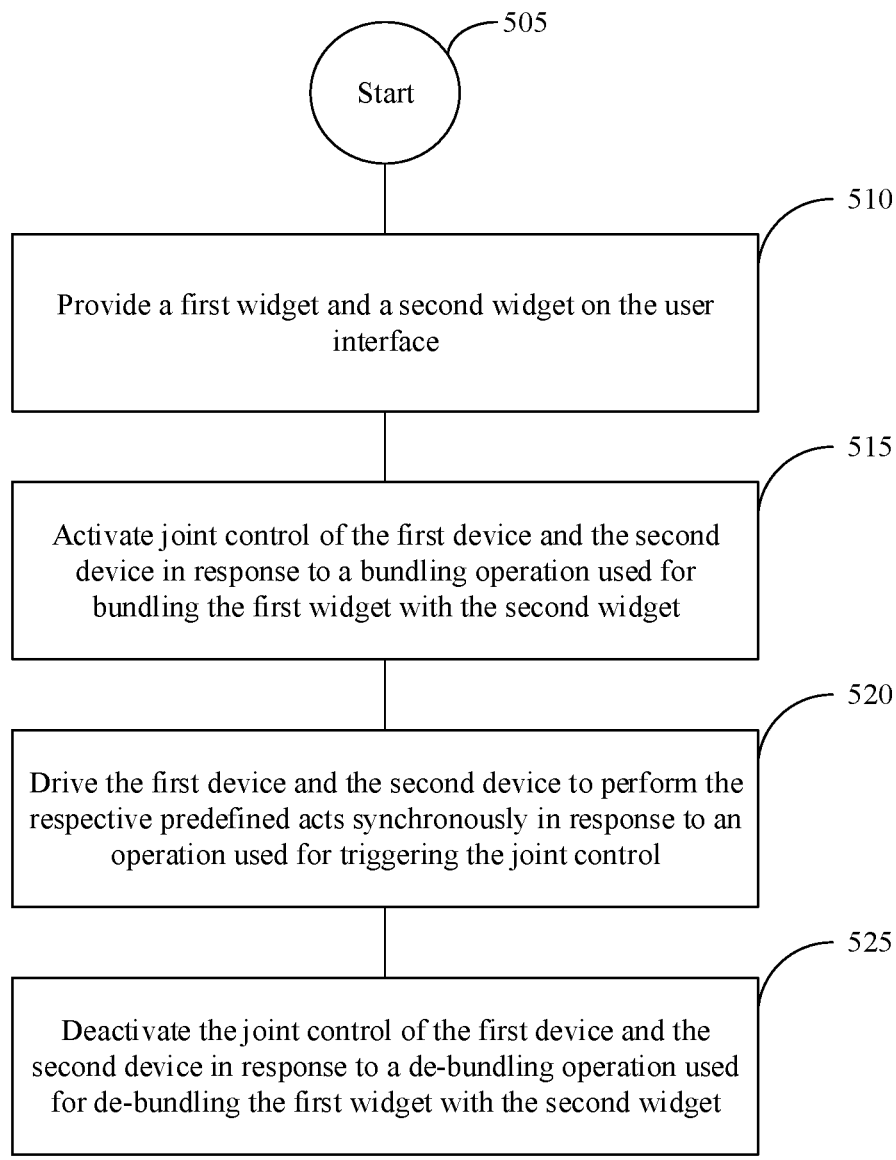
FIG. 5 illustrates an exemplary process 500 according to some embodiments.

Based on the embodiments of FIG. 4, FIG. 5 illustrates an exemplary process 500 of user terminal 105. Those content similar to the embodiments of FIG. 4 may refer to the embodiments as described above and will be omitted herein for brevity. Process 500 begins at step 505.

At step 510, the user terminal 105 provides a first widget and a second widget on the user interface, where the first widget is associated with control of the first device, and the second widget is associated with control of the second device.

At step 515, the user terminal 105 activates joint control of the first device and the second device in response to a bundling operation used for bundling the first widget with the second widget.

At step 520, the user terminal 105 drives, in response to an operation used for triggering the joint control, the first device and the second device to perform the respective predefined acts synchronously.

At step 525, the user terminal 105 deactivates the joint control of the first device and the second device in response to a de-bundling operation used for de-bundling the first widget with the second widget.

In some embodiments, step 525 is performed by providing, in response to an operation used for de-bundling the first widget with the second widget, a visual de-bundling indicator on the user interface, where the visual de-bundling indicator indicates deactivating the joint control of the first device and the second device.

The operation used for de-bundling the first widget with the second widget is also referred to as a de-bundling operation hereafter. The visual de-bundling indicator used for indicating deactivating joint control of the first device and the second device is also referred to as a de-bundling indicator hereafter.

In some embodiments, the de-bundling operation includes a long-press operation and a dragging operation. For example, the user terminal 105 displays, upon detecting a long-press operation with respect to the bundling indicator, the first and second widget separately; further detects that an icon corresponding to the first widget is dragged away from an icon corresponding to the second widget within a preset range and, accordingly, determines the dragging operation as a de-bundling operation. Details of the long-press and dragging operations may further refer to the description of FIG. 6 below.

In some embodiments, the de-bundling operation includes a check-box operation. For example, the user terminal 105 detects a cancel operation on a check box of the first widget and stops highlighting of the icon corresponding to the first widget. Similarly, the user terminal 105 detects a cancel operation on a check box of the second widget and stops highlighting of the icon corresponding to the second widget. Details of the check-box operation may further refer to the description of FIG. 8 below.

In some embodiments, the de-bundling operation is able to be implemented in any suitable manner. For example, in addition to the long-press and dragging operations and check-box operation described above, the de-bundling operation may further include dragging any one of the first and second widgets out of a predefined area on the user interface.

In some embodiments, the de-bundling indicator varies depending on the implementation manner of the de-bundling operation. For example, when the de-bundling operation is implemented through the long-press and dragging operations as described above, the de-bundling indicator may include restoring display of the first widget and the second widget to a state prior to generating the bundling indicator. For another example, when the de-bundling operation is implemented through the check-box operation as described above, the de-bundling indicator may include stopping the highlighting of both the first and second widgets. In other words, the de-bundling indicator may be displayed on the user interface in any suitable manner as long as the display manner thereof is able to clearly represent to the human user the deactivation of the joint control of the first and second devices.

Moreover, step 525 is described above as providing the visual de-bundling indicator, but the disclosure is not limited thereto. In some embodiments, the de-bundling of the first widget and the second widget is also implementable at the background of the user terminal 105 without displaying any visual indicator. For example, after receiving a de-bundling operation on the user interface, the user terminal 105 may inform the human user of the de-bundling by playing a preset voice message, so as to indicate deactivation of the joint control of the first device and the second device. Details thereof will be omitted here for brevity.

According to at least some embodiments of the disclosure, multiple devices communicated with and bundled by the user terminal can be de-bundled in response to the de-bundling operation as received. In this way, joint control of the multiple devices can be activated and deactivated flexibly as required without necessity to design complex interfaces between these toys or learn difficult operations caused thereby.

Figure 6:
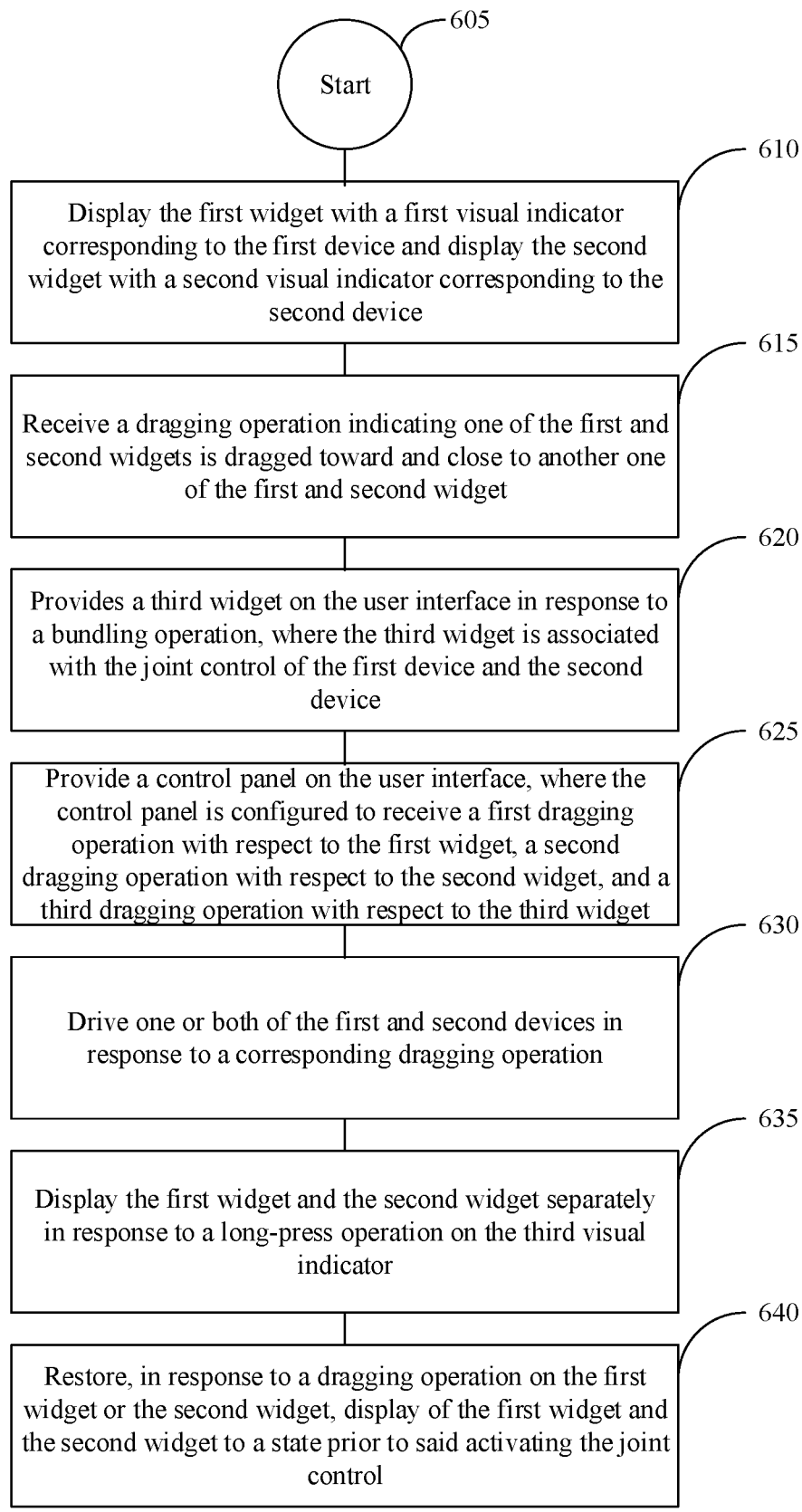
FIG. 6 illustrates an exemplary process 600 according to some embodiments.

Based on the embodiments of FIG. 4 and FIG. 5, FIG. 6 illustrates an exemplary process 600 of user terminal 105. Those content similar to the embodiments of FIG. 4 and FIG. 5 may refer to the embodiments as described above and will be omitted herein for brevity. Process 600 begins at step 605.

At step 610, the user terminal 105 displays the first widget with a first visual indicator corresponding to the first device and displays the second widget with a second visual indicator corresponding to the second device.

In some embodiments, the first and second visual indicators are displayed in a manner corresponding to the first and second devices, respectively, such that a human user is illustratively indicated to operates on the first visual indicator when he/she intends to drive the first device, and operates on the second visual indicator when he/she intends to drive the second device. In other words, the first visual indicator and the second visual indicator may be displayed in any suitable manner as long as they are able to be distinguishable from each other. For example, each of the first and second visual indicators includes a toy icon, a name, a battery icon, an act icon, a user id, a user profile picture and the like.

Figure 7A:
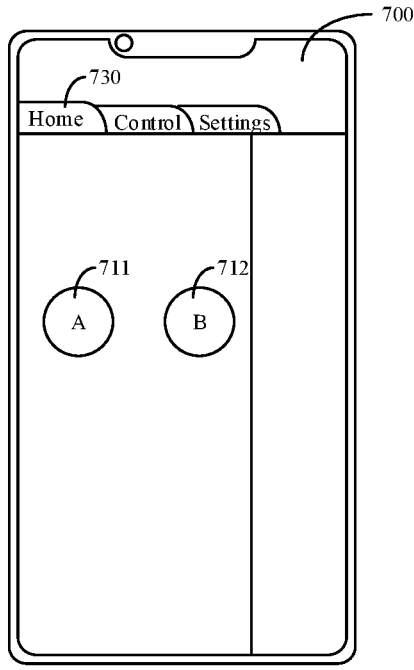

FIG. 7A illustrates an example of the user interface 700 provided by the user terminal 105. In this example, the first visual indicator 711 is a toy icon (marked as "A" in the drawing) corresponding to the first device, and the second visual indicator 712 is a toy icon (marked as "B" in the drawing) corresponding to the second device.

At step 615, the user terminal 105 receives a dragging operation indicating one of the first and second widgets is dragged toward and close to another one of the first and second widget.

Taking the first widget as example, the user terminal may first receive a long-press operation on the first widget and, then, detect that the first widget is dragged toward the second widget. In the process of dragging operation, upon determining that a distance between the first widget and the second widget falls within a preset range, the user terminal determines the dragging operation as a bundling operation.

It should be noted that, a widget and a visual indicator of the widget are used exchangeably in this disclosure. For example, receiving a long-press operation with respect to the first widget is equivalent to receiving the long-press operation with respect to the first visual indicator.

Figure 7B:
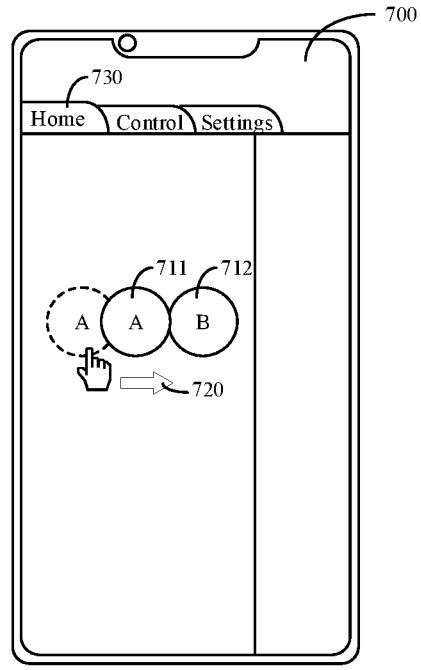

Now referring to FIG. 7B, a dragging operation (marked as an arrow 720 in the drawing) is detected on the user interface 700, and the first visual indicator 711 is dragged toward and sufficiently close to (e.g., overlapping with) the second visual indicator 712.

At step 620, the user terminal 105 provides a third widget on the user interface in response to a bundling operation, where the third widget is associated with the joint control of the first device and the second device.

In some embodiments, after receiving the bundling operation, the user terminal 105 binds the control of first and second devices together. In other words, instead of or in addition to drive the first and second devices through the first and second widgets, respectively, the user terminal 105 is able to generate a control signal set, including control signals with respect to the first and second devices, in response to a joint-control operation. Accordingly, the user terminal 105 provides the third widget for the human user to apply the joint-control operation.

In some embodiments, similarly as the first and second widgets, the third widgets is able to receive a control operation with respect to the first and second devices. For example, when the third widget is dragged (e.g., upward/downward) within the user interface, a magnitude of level at which the first and second devices are driven is adjusted accordingly (e.g., increased/decreased).

In some embodiments, the third widget varies depending on the implementation manner of the bundling operation. For example, when the bundling operation is implemented through the dragging operation as described above, the third widget may include an icon, which is different from any one of the first and second widgets, but is not limited thereto. The third widget may be displayed on the user interface in any suitable manner as long as the display manner thereof is able to clearly represent to the human user the association between it and the joint control of the first and second devices.

Figure 7C:
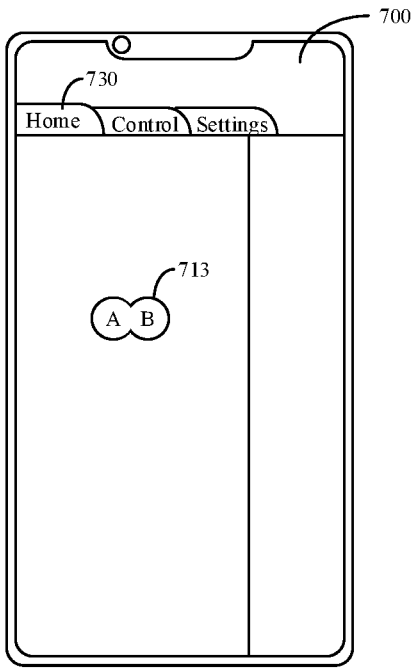

Now referring to FIG. 7C, after determining the dragging operation (marked as the arrow 720 in FIG. 7B) as a bundling operation, the user terminal 105 provides a third visual indicator 713 (corresponding to the third widget) associated with the joint control of the first device and the second device.

As described above, the number of devices and corresponding widgets is not limited to two, but may be three and more. Accordingly, the number of the third widget may be more than one. For example, there are four adult toys to be controlled, and the user terminal 105 provides four widgets on the user interface corresponding to the four adult toys, respectively. Upon receiving one or more bundling operations, the user terminal 105 may display two additional widgets on the user interface, with one corresponding to two of the four adult toys, and the other one corresponding to remaining two of the four adult toys.

At step 625, the user terminal 105 provides a control panel on the user interface, where the control panel is configured to receive a first dragging operation with respect to the first widget, a second dragging operation with respect to the second widget, and a third dragging operation with respect to the third widget.

In some embodiments, at least one of the first widget, the second widget and the third widget are displayed within the control panel, for example, in the form of a circle (also referred to as "control ball"); and the control ball(s) corresponding to the widget(s) is used for, in response to a sliding/dragging operation, triggering the user terminal 105 to generate corresponding signals for driving the device(s).

Figure 7D:
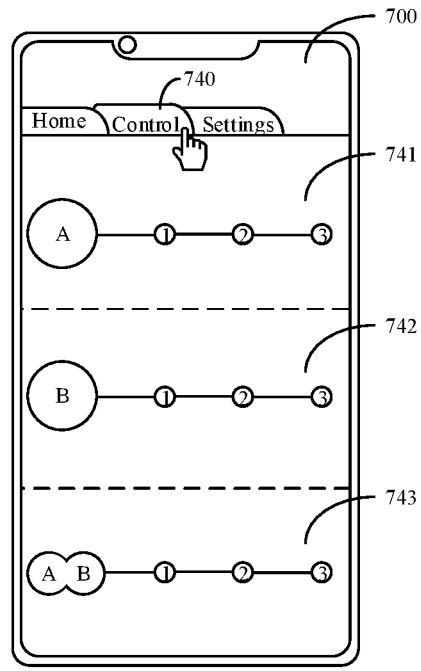

FIG. 7D illustrates an example of the control panel 740. As shown in FIG. 7D, the control panel 740 may be a predefined area within the user interface 700, in which the first visual indicator 711, the second visual indicator 712 and the third visual indicator 713 are separately displayed.

In some embodiments, the control panel 740 is also the area where the bundling operation is received and the third visual indicator 713 is generated. Alternatively, in some embodiments, the control panel 740 is independent of another panel (e.g., main panel 730 as shown in FIG. 7C) where the bundling operation is received and the third visual indicator 713 is generated. For example, after the third visual indicator 713 is generated and displayed as shown in FIG. 7C, the human user of the user terminal 105 may click on the label corresponding to the control panel 740, so as to switch the display of user interface 700 to the control panel 740 as shown in FIG. 7D.

Referring to FIG. 7D, the control panel 740 further includes first to third operation areas 741, 742 and 743 corresponding to the first to third visual indicators 711, 712 and 713, respectively. The first operation area 741 is used for receiving the first dragging operation with respect to the first widget, the second operation area 742 is used for receiving the second dragging operation with respect to the second widget, and the third operation area 743 is used for receiving the third dragging operation with respect to the third widget.

Moreover, each of the first to third operation areas 741, 742 and 743 may be divided into multiple segments corresponding to different levels of predefined acts of the first device and/or the second device. As shown in FIG. 7D, each of the first to third operation areas 741, 742 and 743 is displayed with three segments, indicating both the first and second devices can be driven to perform their predefined acts in three different levels.

In some embodiments, any of the first to third operation areas 741, 742 and 743 may receive dragging operations in different directions. For example, the first device includes two motors; a dragging operation along with one direction (e.g., long-side direction of user interface 700 in the drawing) corresponds to one motor, and a dragging operation along with another direction (e.g., short-side direction of user interface 700 in the drawings) corresponds to the other motor. For another example, the first device may be controlled in two dimensions (e.g., amplitude and frequency); a dragging operation along with one direction corresponds to one dimension (e.g., amplitude), and a dragging operation along with another direction corresponds to the other dimension (e.g., frequency).

At step 630, the user terminal 105 drives one or both of the first and second devices in response to a corresponding dragging operation.

In some embodiments, the user terminal 105 drives, in response to the first dragging operation, the first device to perform a first predefined act at a first level. For example, as shown in FIG. 7E, upon receiving a dragging operation (marked as arrow 751 in the drawing) within the first operation area 741, the user terminal 105 generates and transmits a control signal, which is used for driving the first device to perform the first predefined act (e.g., vibration) at level one.

In some embodiments, the user terminal 105 drives, in response to the second dragging operation, the second device to perform a second predefined act at a second level. For example, as shown in FIG. 7E, upon receiving a dragging operation (marked as arrow 752 in the drawing) within the second operation area 742, the user terminal 105 generates and transmits a control signal, which is used for driving the second device to perform the second predefined act (e.g., rotation) at level two.

In some embodiments, the user terminal 105 drives, in response to the third dragging operation, the first device to perform the first predefined act and the second device to perform the second predefined act at a same level. For example, as shown in FIG. 7E, upon receiving a dragging operation (marked as arrow 753 in the drawing) within the third operation area 743, the user terminal 105 generates and transmits a control signal set, which is used for driving the first and second devices to perform their respective predefined acts at level three.

In some embodiments, a magnitude of the level is proportional to an operation distance of the dragging operation, each magnitude of different level corresponding to each value of at least one parameter selected from a group including amplitude, frequency, speed, acceleration, temperature, and any combinations thereof.

At step 635, the user terminal displays, in response to a long-press operation on the third visual indicator, the first widget and the second widget separately.

At step 640, the user terminal restores, in response to a dragging operation on the first widget or the second widget, display of the first widget and the second widget to a state prior to said activating the joint control.

Steps 635 and 640 correspond to step 525 as described above. Specifically, the long-press operation and the dragging operation herein constitute a de-bundling operation in step 525. For those details omitted here, the description of FIG. 5 may be referred to.

In some embodiments, the de-bundling operation may be received by the control panel 740. Alternatively, in some embodiments, the de-bundling operation is to be received by a main panel independent of the control panel. For example, after performing the joint control of the first and second devices through the control panel 740, the human user of the user terminal 105 may click on the label corresponding to the main panel 730, so as to switch the display of user interface 700 back to the main panel 730 as shown in FIG. 7C.

Upon receiving the long-press operation on the third visual indicator 713 though the main panel 730, the user terminal displays the first widget and the second widget separately, as shown in FIG. 7F.

Further, upon receiving a dragging operation on the first widget or the second widget as separately displayed, the user terminal 105 restores display of the first widget and the second widget to a state prior to generating the third visual indicator. For example, as shown in FIG. 7F, upon detecting a dragging operation (marked as arrow 760 in the drawing) applying on the first visual indicator 711 away from the second visual indicator 712, the user terminal 105 determines such dragging operation as a de-bundling operation. Accordingly, the user terminal 105 restores display of first visual indicator 711 and the second visual indicator 712 to a state prior to generating the third visual indicator 713, for example, to a state as shown in FIG. 7A.

Figure 8:
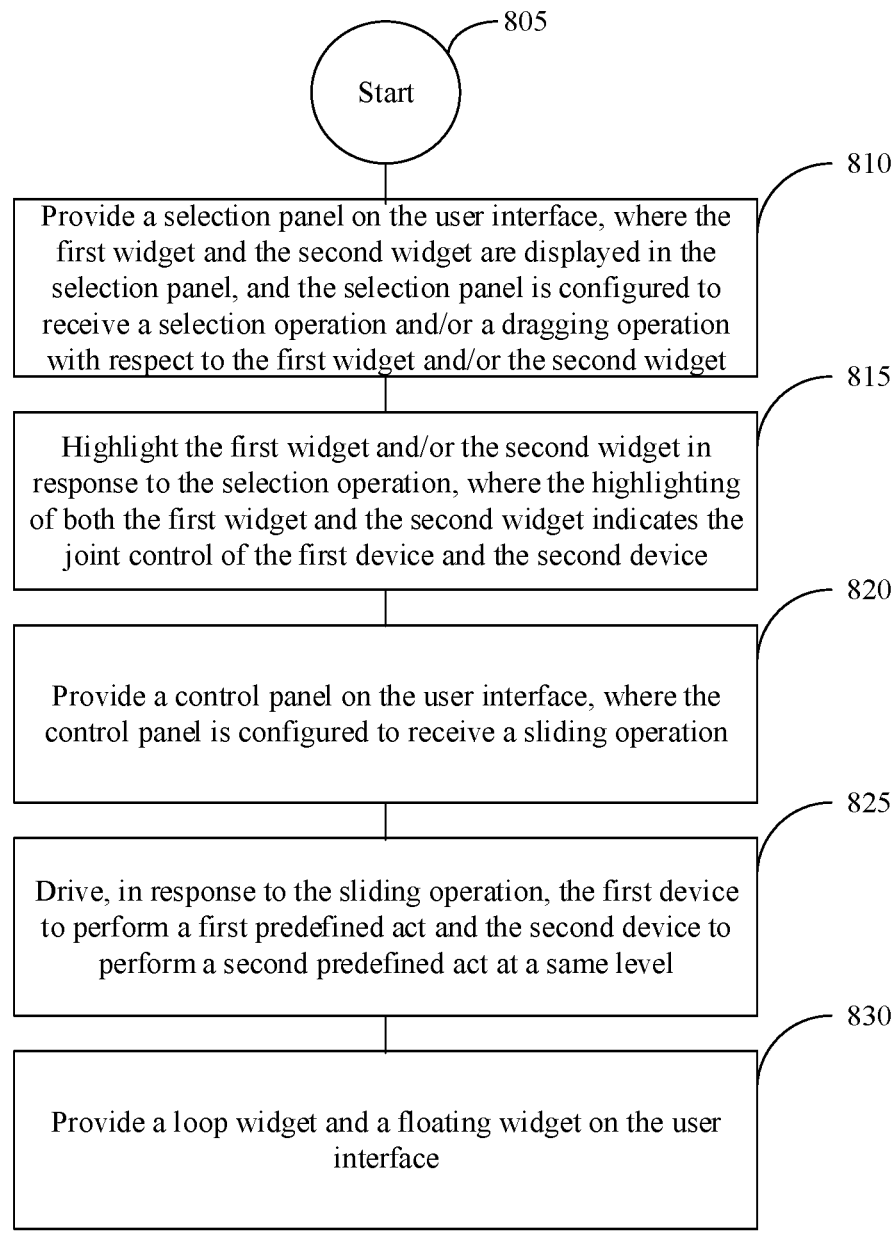
FIG. 8 illustrates an exemplary process 800 according to some embodiments.

Based on the embodiments of FIG. 4 and FIG. 5, FIG. 8 further illustrates an exemplary process 800 of user terminal 105. Those content similar to the embodiments of FIG. 4 and FIG. 5 may refer to the embodiments as described above and will be omitted herein for brevity. Process 800 begins at step 805.

At step 810, the user terminal 105 provides a selection panel on the user interface, where the first widget and the second widget are displayed in the selection panel, and the selection panel is configured to receive at least one of a selection operation or a dragging operation with respect to at least one of the first widget and the second widget.

In some embodiments, the first and second widgets are displayed in the selection panel corresponding to the first and second devices, respectively, such that a human user is illustratively indicated to operates on the first widget when he/she intends to drive the first device, and operates on the second widget when he/she intends to drive the second device. In other words, the first widget and the second widget may be displayed in any suitable manner as long as they are able to be distinguishable from each other. For example, each of the first and second widgets is displayed with a toy icon, a name, a battery icon, an act icon, a user id, a user profile picture and the like.

Figure 9A:
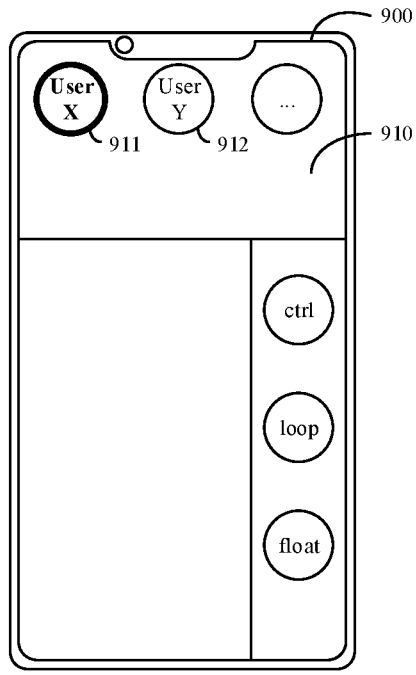
FIG. 9A to FIG. 9D illustrate an exemplary user interface 900 provided by the user terminal 105.

FIG. 9A illustrates an example of the user interface 900 provided by the user terminal 105. In the selection panel 910 shown in FIG. 9A, the first widget 911 is displayed with a user id (marked as "User X" in the drawing) corresponding to the first device, and the second widget 912 is displayed with another user id (marked as "User Y" in the drawing) corresponding to the second device.

It should be noted that, FIG. 9A is described for illustrating an example of the disclosure, rather than limiting the scope thereof. In some other embodiments, three or more widgets corresponding to three or more devices of different users may be displayed. Moreover, the communication connections between the user terminal 105 and the three or more devices may be established via any suitable short distance technique such as WiFi, Bluetooth, ZigBee, NFC, IrDA; and/or established via another user terminal. For example, the first device of User X and the second device of User Y are located near the user terminal 105 and, thus, may be connected with the user terminal 105 via any suitable short distance technique. For another example, an additional widget (not shown) may be displayed with another user id (e.g., User Z) corresponding to a third device, which is located remotely from the user terminal 105. Accordingly, the third device may be connected with and controlled by the user terminal 105 via a user terminal of User Z, while the third device is further connected with the user terminal of User Z via any suitable short distance technique.

The selection panel 910 is used for receiving the bundling operation, including for example a selection operation, which will be described in step 815 here after.

At step 815, the user terminal 105 highlights, in response to the selection operation, the at least one of the first widget and the second widget, where the highlighting of both the first widget and the second widget indicates the joint control of the first device and the second device.

Herein, the selection operation corresponds to the checkbox operation as described above in the embodiments of step 415, which means the first and second widgets can be selected individually or together.

Figure 9B:
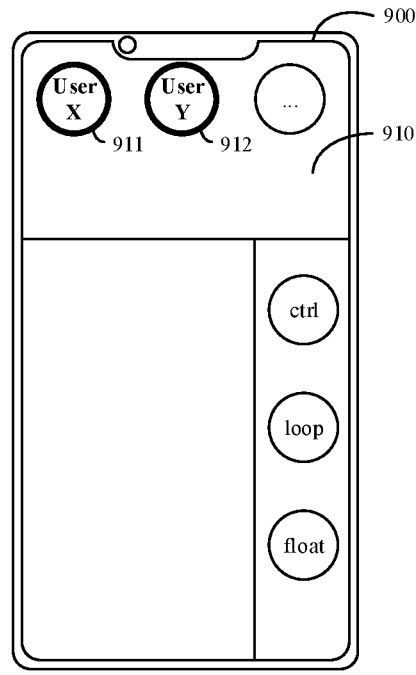

For example, as shown in FIG. 9A, the first widget 911 is firstly selected and highlighted (exemplified as being boldened in the drawing). Subsequently, as shown in FIG. 9B, the second widget 912 is further selected and also highlighted. The highlighting of both the first widget and the second widget indicates the joint control of the first device and the second device. In other words, the highlighting of both the first widget and the second widget may be considered as a bundling indicator as described above.

Accordingly, a corresponding de-bundling operation may include stopping the highlighting of both the first widget and the second widget, which may be caused by cancelling the selection of any one of the first and second widgets. Detail thereof will be omitted herein for brevity.

It should be noted that, the selection operation performed on both the first widget and the second widget in step 815 may be understood as the bundling operation of step 415 in the forgoing embodiments, but the disclosure is not limited thereto. In some embodiments, the first and second widgets 911, 912 displayed in the selection panel 910 are also able to receive a dragging operation as the bundling operation and, after being bundled, receive a combination of long-press and dragging operation as the de-bundling operation.

Taking the first widget 911 as example, the user terminal 105 may detect that the first widget 911 is dragged toward the second widget 912. In the process of dragging operation, upon determining that a distance between the first widget 911 and the second widget 912 falls within a preset range, the user terminal 105 determines the dragging operation as a bundling operation. Details of the dragging operation may refer to the description of FIG. 6, and will not be repeated herein for brevity.

In some embodiments, the first and second widgets 911, 912 displayed in the selection panel 910 are not used for receiving any dragging operation to control the first and second devices. The control of first and second devices in these embodiments will be discussed as follows.

At step 820, the user terminal 105 provides a control panel on the user interface, where the control panel is configured to receive a sliding operation.

Figure 9C:
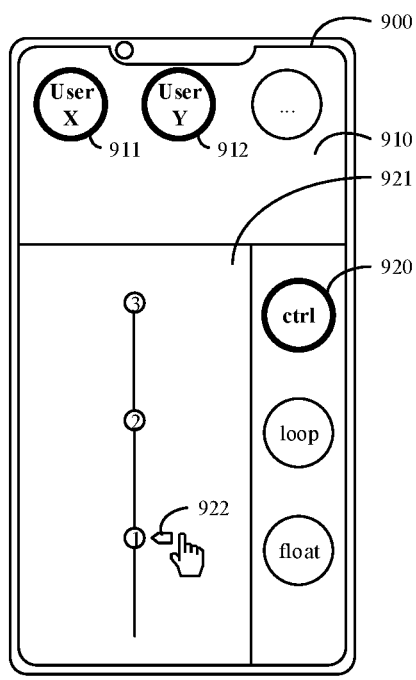

FIG. 9C illustrates an example of the control panel 920. As shown in FIG. 9C, the control panel 920 is a display area adjacent to the selection panel 910, but the disclosure is not limited thereto. In some other embodiments, the control panel 920 may be a display area that is activated independently of the selection panel 910, similar as what is shown in FIG. 7C and FIG. 7D.

Referring to FIG. 9C, the control panel 920 further includes an operation area 921 used for receiving the sliding operation with respect to joint control of the first and second devices.

At step 825, the user terminal 105 drives, in response to the sliding operation, the first device to perform a first predefined act and the second device to perform a second predefined act at a same level.

In some embodiments, the first and second widgets are not displayed in the control panel, and the sliding operation is to be performed on another widget displayed therein. For example, as shown in FIG. 9C, the first and second widgets 911, 912 are not displayed in the operation area 921, and a slide widget 922 is used for receiving the sliding operation.

Further referring to FIG. 9C, the operation area 921 may be divided into multiple segments corresponding to different levels of the joint control. As shown in FIG. 9C, the operation area 921 is displayed with three segments, indicating the joint control of the first and second devices can be implemented in three different levels.

In some embodiments, the sliding operation includes free sliding without limitation on the sliding direction, or limited sliding along with a fixed track (e.g., along with the long-side direction or short-side direction in the drawing).

In some embodiments, a magnitude of the level is proportional to an operation distance of the sliding operation, each magnitude of different level corresponding to each value of at least one parameter selected from a group including amplitude, frequency, speed, acceleration, temperature, and any combinations thereof.

At step 830, the user terminal 105 provides a loop widget and a floating widget on the user interface.

In some embodiments, the loop widget is used for activating a loop mode in response to a selection operation; and in the loop mode, a control pattern corresponding to a control operation with respect to at least one of the first device and the second device is recorded and, after the control operation is terminated, is playback.

In some embodiments, the floating widget is used for activating a floating mode in response to a selection operation; and in the floating mode, a level corresponding to a control operation with respect to at least one of the first device and the second device is held until receiving a cancel-selection operation on the floating widget.

Figure 9D:
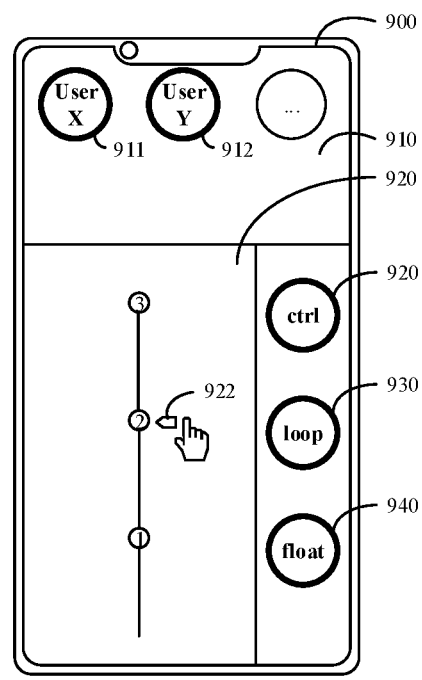

In some embodiments, the loop mode and the floating mode are able to be in activation synchronously. FIG. 9D illustrates an example of the loop widget 930 and floating widget 940. As shown in FIG. 9D, the loop widget 930 and floating widget 940 are adjacent to the control panel 920 and displayed in a state of being selected at the same time.

Figure 10:
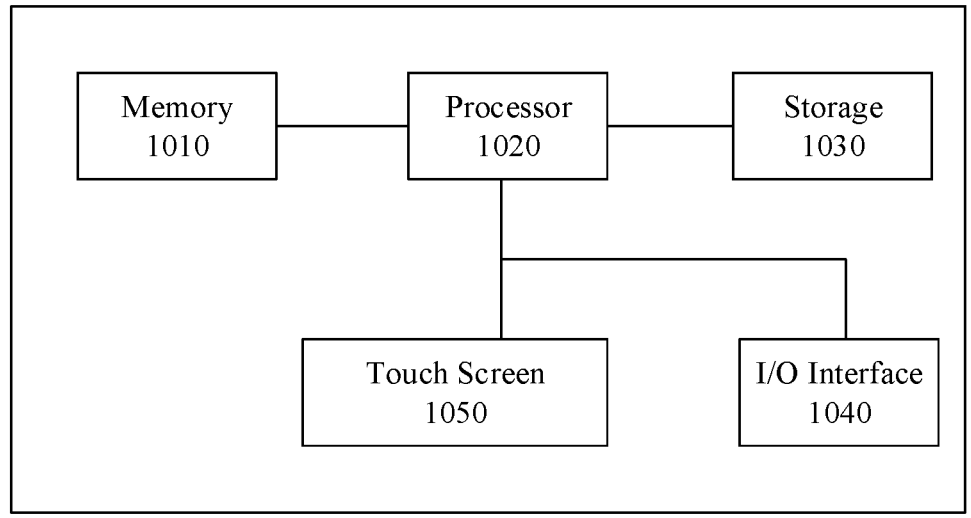
FIG. 10 is a block diagram of an exemplary user terminal 1000 according to some embodiments.

FIG. 10 is a block diagram of an exemplary user terminal 1000 according to some embodiments of the present application. User terminal 1000 includes a memory 1010, a processor 1020, a storage 1030, an I/O interface 1040, and a touch screen 1050. One or more of these elements of user terminal 1000 may be included for performing any embodiment of the method as described above. User terminal 105 shown in FIG. 1 may be configured as user terminal 1000.

Processor 1020 includes any appropriate type of general-purpose or special-purpose microprocessor, digital signal processor, or microcontroller. Processor 1020 can be one of processors in user terminal 105. Memory 1010 and storage 1030 may include any appropriate type of mass storage provided to store any type of information that processor 1020 may need to operate. Memory 1010 and storage 1030 may be a volatile or non-volatile, magnetic, semiconductor, tape, optical, removable, non-removable, or other type of storage device or tangible (i.e., non-transitory) computer-readable medium including, but not limited to, a read-only memory (ROM), a flash memory, a dynamic random-access memory (RAM), and a static RAM. Memory 1010 and/or storage 1030 may be configured to store one or more programs for execution by processor 1020 to perform any embodiment of the method, as disclosed herein.

Memory 1010 and/or storage 1030 may be further configured to store information and data used by processor 1020.

I/O interface 1040 may be configured to facilitate the communication between user terminal 1000 and other apparatuses. For example, I/O interface 1040 may receive a signal from another apparatus (e.g., a corresponding sex toy). I/O interface 1040 may also output signal to other apparatuses.

Touch screen 1050 may be configured to provide user interface to the human user and receive control operation from the human user for controlling any device connected thereto.

Processor 1020 can be configured to performs operations including: providing, through the touch screen 1050, a first widget and a second widget on the user interface, where the first widget is associated with control of the first device, and the second widget is associated with control of the second device; activating joint control of the first device and the second device in response to a bundling operation used for bundling the first widget with the second widget; and driving, in response to an operation used for triggering the joint control, the first device and the second device to perform the respective predefined acts synchronously.

In some embodiments, the first device is a first adult toy, and the second device is a second adult toy.

In some embodiments, the first device is a part of the first adult toy, and the second device is a part of the second adult toy.

In some embodiments, the first device is a part of the first adult toy, and the second device is another part of the first adult toy.

In some embodiments, processor 1020 can be also configured to receive a touch control operation performed on at least one of the first widget and the second widget as the bundling operation.

In some embodiments, processor 1020 can be also configured to receive a dragging operation indicating one of the first and second widgets is dragged toward and close to another one of the first and second widget; and provide a third widget on the user interface, where the third widget is associated with the joint control of the first device and the second device.

In some embodiments, processor 1020 can be also configured to display the first widget with a first visual indicator corresponding to the first device; display the second widget with a second visual indicator corresponding to the second device; and display the third widget with a third visual indicator corresponding to the first device and the second device.

In some embodiments, processor 1020 can be also configured to deactivate the joint control of the first device and the second device in response to a de-bundling operation used for de-bundling the first widget with the second widget.

In some embodiments, processor 1020 can be also configured to display the first widget and the second widget separately in response to a long-press operation on a third widget, where the third widget is associated with the joint control of the first device and the second device; and restore, in response to a dragging operation on the first widget or the second widget, display of the first widget and the second widget to a state prior to said activating the joint control.

In some embodiments, processor 1020 can be also configured to provide a control panel on the user interface, where the control panel is configured to receive a first dragging operation with respect to the first widget, a second dragging operation with respect to the second widget, and a third dragging operation with respect to a third widget, where the third widget is associated with the joint control of the first device and the second device; and drive, in response to the first dragging operation, the first device to perform a first predefined act at a first level; or drive, in response to the second dragging operation, the second device to perform a second predefined act at a second level; or drive, in response to the third dragging operation, the first device to perform the first predefined act and the second device to perform the second predefined act at a same level, where a magnitude of the level is proportional to an operation distance of the dragging operation, each magnitude of different level corresponding to each value of at least one parameter selected from a group comprising amplitude, frequency, speed, acceleration, temperature, and any combinations thereof.

In some embodiments, processor 1020 can be also configured to provide a selection panel on the user interface, where the first widget and the second widget are displayed in the selection panel, and the selection panel is configured to receive at least one of a selection operation or a dragging operation with respect to at least one of the first widget and the second widget; and highlight, in response to the selection operation, the at least one of the first widget and the second widget, where highlighting of both the first widget and the second widget indicates the joint control of the first device and the second device; or display, in response the dragging operation reducing a distance between the first widget and the second widget in the selection panel, a third widget in the selection panel, where the third widget indicates the joint control of the first device and the second device.

In some embodiments, processor 1020 can be also configured to provide a control panel on the user interface, where the control panel is configured to receive a sliding operation; and drive, in response to the sliding operation, the first device to perform a first predefined act and the second device to perform a second predefined act at a same level, where a magnitude of the level is proportional to an operation distance of the sliding operation, each magnitude of different level corresponding to each value of at least one parameter selected from a group comprising amplitude, frequency, speed, acceleration, temperature, and any combinations thereof.

In some embodiments, processor 1020 can be also configured to providing a loop widget and a floating widget on the user interface; activating a loop mode in response to a selection operation on the loop widget, where, in the loop mode, a control pattern corresponding to a control operation with respect to at least one of the first device and the second device is recorded and, after the control operation is terminated, is playback; and activating a floating mode in response to a selection operation on the floating widget, where, in the floating mode, a level corresponding to the control operation is held until receiving a cancel-selection operation on the floating widget, where the loop mode and the floating mode are able to be in activation synchronously.

Figure 11:
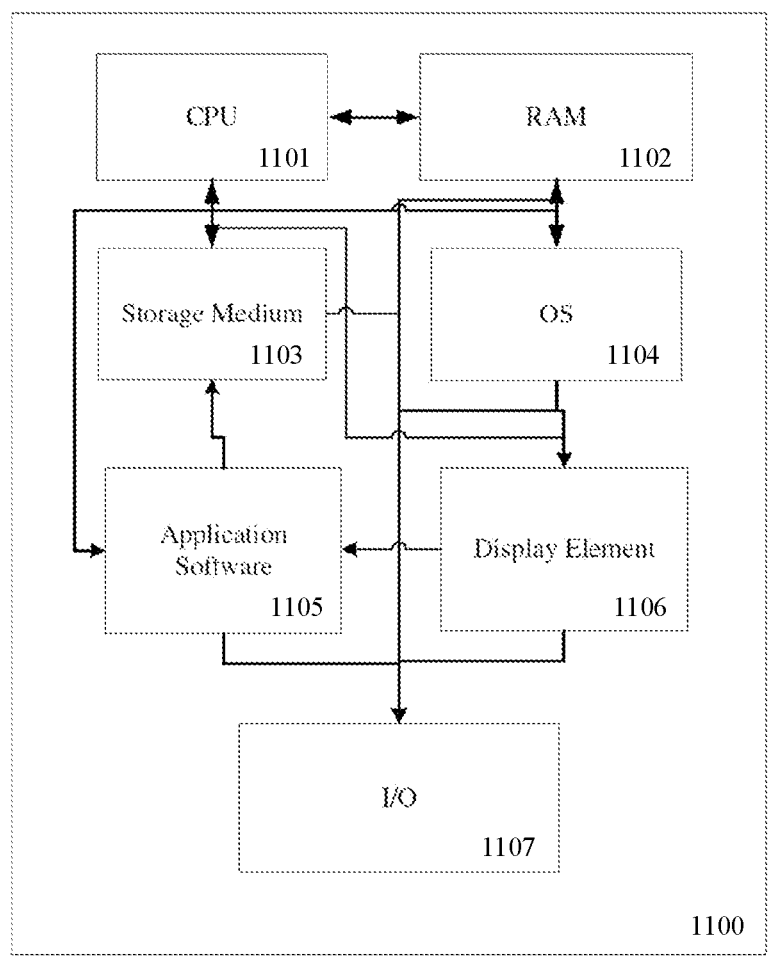
FIG. 11 is a schematic illustration of an exemplary user terminal according to some embodiments.

An illustrative representation of a user terminal appropriate for use with embodiments of the present disclosure is shown in FIG. 11. The user terminal 1100 can generally be comprised of a Central Processing Unit (CPU, 1101), optional further processing units including a graphics processing unit (GPU), a Random Access Memory (RAM, 1102), a mother board 1103, or alternatively/additionally a storage medium (e.g., hard disk drive, solid state drive, flash memory, cloud storage), an operating system (OS, 1104), one or more application software 1105, a display element 1106, and one or more input/output devices/means 1107, including one or more communication interfaces (e.g., RS232, Ethernet, WiFi, Bluetooth, USB). Useful examples include, but are not limited to, personal computers, smart phones, laptops, mobile computing devices, tablet PCs, touch boards, and servers. Multiple user terminals can be operably linked to form a computer network in a manner as to distribute and share one or more resources, such as clustered computing devices and server banks/farms.

Various examples of such general-purpose multi-unit computer networks are suitable for embodiments of the disclosure, their typical configuration and many standardized communication links are well known to one skilled in the art, which is omitted herein for brevity.

According to an exemplary embodiment of the present disclosure, data may be transferred to the system, stored by the system and/or transferred by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present disclosure are contemplated for use with any configuration.

In general, the methods provided herein may be employed by a user of a user terminal whether connected to a network or not. While such components/modules are offline, and the data they generated will then be transmitted to the relevant other parts of the system once the offline component/module comes again online with the rest of the network (or a relevant part thereof). According to an embodiment of the present disclosure, some of the applications of the present disclosure may not be accessible when not connected to a network, however a user or a module/component of the system itself may be able to compose data offline from the remainder of the system that will be consumed by the system or its other components when the user/offline system component or module is later connected to the system network.

Another aspect of the disclosure is directed to a non-transitory computer-readable medium storing instructions which, when executed, cause one or more processors to perform methods, consistent with the embodiments disclosed herein. The computer-readable medium may include volatile or non-volatile, magnetic, semiconductor, tape, optical, removable, non-removable, or other types of computer-readable medium or computer-readable storage devices. For example, the computer-readable medium may be a storage device or a memory module having the computer instructions stored thereon, as disclosed. In some embodiments, the computer-readable medium may be a disc or a flash drive having the computer instructions stored thereon.

It will be appreciated that the present disclosure is not limited to the exact construction that has been described above and illustrated in the accompanying drawings, and that various modifications and changes can be made without departing from the scope thereof. It is intended that the scope of the application should only be limited by the appended claims.

What is claimed is:

1. A method for controlling devices, implemented by a user terminal, wherein the user terminal comprises a user interface and is in communication with a first device and a second device, the first device and the second device are configured to perform respective predefined acts sexually stimulating one or more human users, and the method comprises:
    providing a first widget and a second widget on the user interface, wherein the first widget is associated with control of the first device, and the second widget is associated with control of the second device;

activating joint control of the first device and the second device in response to a bundling operation used for bundling the first widget with the second widget; and driving, in response to an operation used for triggering the joint control, the first device and the second device to perform the respective predefined acts synchronously, wherein said activating the joint control of the first device and the second device in response to the bundling operation comprises:

receiving a dragging operation indicating one of the first and second widgets is dragged toward and close to another one of the first and second widget; and providing a third widget on the user interface, wherein the third widget is associated with the joint control of the first device and the second device.

2. The method of claim 1, further comprising:
receiving a touch control operation performed on at least one of the first widget and the second widget as the bundling operation.

3. The method of claim 1, further comprising:
displaying the first widget with a first visual indicator corresponding to the first device;
displaying the second widget with a second visual indicator corresponding to the second device; and
displaying the third widget with a third visual indicator corresponding to the first device and the second device.

4. The method of claim 1, further comprising:
deactivating the joint control of the first device and the second device in response to a de-bundling operation used for de-bundling the first widget with the second widget.

5. The method of claim 4, wherein said deactivating the joint control of the first device and the second device in response to the de-bundling operation comprises:
displaying the first widget and the second widget separately in response to a long-press operation on the third widget; and
restoring, in response to a dragging operation on the first widget or the second widget, display of the first widget and the second widget to a state prior to said activating the joint control.

6. The method of claim 1, further comprising:
providing a control panel on the user interface, wherein the control panel is configured to receive a first dragging operation with respect to the first widget, a second dragging operation with respect to the second widget, and a third dragging operation with respect to the third widget; and
driving, in response to the first dragging operation, the first device to perform a first predefined act at a first level; or driving, in response to the second dragging operation, the second device to perform a second predefined act at a second level; or driving, in response to the third dragging operation, the first device to perform the first predefined act and the second device to perform the second predefined act at a same level, wherein a magnitude of each of the first and second levels is proportional to an operation distance of each of the first and second dragging operations, the magnitude of each of the first and second levels corresponding to a value of at least one parameter selected from a group comprising amplitude, frequency, speed, acceleration, temperature, and any combinations thereof.

7. The method of claim 1, wherein said activating the joint control of the first device and the second device in response to the bundling operation comprises:

providing a selection panel on the user interface, wherein the first widget and the second widget are displayed in the selection panel, and the selection panel is configured to receive at least one of a selection operation or a dragging operation with respect to at least one of the first widget and the second widget; and highlighting, in response to the selection operation, the at least one of the first widget and the second widget, wherein the highlighting of both the first widget and the second widget indicates the joint control of the first device and the second device; or displaying, in response to the dragging operation, the third widget in the selection panel, wherein the third widget indicates the joint control of the first device and the second device.

8. The method of claim 7, wherein said driving, in response to the operation used for triggering the joint control, the first device and the second device to perform the respective predefined acts synchronously comprises:
providing a control panel on the user interface, wherein the control panel is configured to receive a sliding operation; and
driving, in response to the sliding operation, the first device to perform a first predefined act and the second device to perform a second predefined act at a level, wherein a magnitude of the level is proportional to an operation distance of the sliding operation, the magnitude of the level corresponding to a value of at least one parameter selected from a group comprising amplitude, frequency, speed, acceleration, temperature, and any combinations thereof.

9. The method of claim 1, further comprising:
providing a loop widget and a floating widget on the user interface;
activating a loop mode in response to a selection operation on the loop widget, wherein, in the loop mode, a control pattern corresponding to a control operation with respect to at least one of the first device and the second device is recorded and, after the control operation is terminated, is played back; and
activating a floating mode in response to a selection operation on the floating widget, wherein, in the floating mode, a level corresponding to the control operation is held until receiving a cancel-selection operation on the floating widget,
wherein the loop mode and the floating mode are able to be in activation synchronously.

10. The method of claim 1, wherein,
the first device is a first adult toy, and the second device is a second adult toy; or
the first device is a part of the first adult toy, and the second device is a part of the second adult toy; or
the first device is a part of the first adult toy, and the second device is another part of the first adult toy.

11. The method of claim 1, wherein the first widget is displayed on the user interface with an icon corresponding to the first device, and the second widget is displayed on the user interface with another icon corresponding to the second device.

12. A user terminal, comprising:
a touch screen, configured to display a user interface;
a communication interface, configured to communicate with a first device and a second device, wherein the first device and the second device are configured to perform respective predefined acts sexually stimulating one or more human users;

a memory, configured to store instructions; and
a processor, wherein the processor is, through executing the instructions, configured to:
provide, through the touch screen, a first widget and a second widget on the user interface, wherein the first widget is associated with control of the first device, and the second widget is associated with control of the second device;
activate joint control of the first device and the second device in response to a bundling operation used for bundling the first widget with the second widget; and
drive, in response to an operation used for triggering the joint control, the first device and the second device to perform the respective predefined acts synchronously,
wherein the processor is further configured to:
receive a dragging operation indicating one of the first and second widgets is dragged toward and close to another one of the first and second widget; and
provide a third widget on the user interface, wherein the third widget is associated with the joint control of the first device and the second device.

13. The user terminal of claim 12, wherein the processor is further configured to:
deactivate the joint control of the first device and the second device in response to a de-bundling operation used for de-bundling the first widget with the second widget.

14. The user terminal of claim 13, wherein the processor is further configured to:
display the first widget and the second widget separately in response to a long-press operation on the third widget; and
restore, in response to a dragging operation on the first widget or the second widget, display of the first widget and the second widget to a state prior to said activating the joint control.

15. The user terminal of claim 12, wherein the processor is further configured to:
provide a control panel on the user interface, wherein the control panel is configured to receive a first dragging operation with respect to the first widget, a second dragging operation with respect to the second widget, and a third dragging operation with respect to the third widget; and
drive, in response to the first dragging operation, the first device to perform a first predefined act at a first level; or drive, in response to the second dragging operation, the second device to perform a second predefined act at a second level; or drive, in response to the third dragging operation, the first device to perform the first predefined act and the second device to perform the second predefined act at a same level,
wherein a magnitude of each of the first and second levels is proportional to an operation distance of each of the first and second dragging operations, the magnitude of each of the first and second levels corresponding to a value of at least one parameter selected from a group comprising amplitude, frequency, speed, acceleration, temperature, and any combinations thereof.

16. The user terminal of claim 12, wherein the processor is further configured to:
provide a selection panel on the user interface, wherein the first widget and the second widget are displayed in the selection panel, and the selection panel is configured to receive at least one of a selection operation or a dragging operation with respect to at least one of the first widget and the second widget; and
highlight, in response to the selection operation, the at least one of the first widget and the second widget, wherein highlighting of both the first widget and the second widget indicates the joint control of the first device and the second device; or
display, in response to the dragging operation, the third widget in the selection panel, wherein the third widget indicates the joint control of the first device and the second device.

17. The user terminal of claim 16, wherein the processor is further configured to:
provide a control panel on the user interface, wherein the control panel is configured to receive a sliding operation; and
drive, in response to the sliding operation, the first device to perform a first predefined act and the second device to perform a second predefined act at a level,
wherein a magnitude of the level is proportional to an operation distance of the sliding operation, the magnitude of the level corresponding to a value of at least one parameter selected from a group comprising amplitude, frequency, speed, acceleration, temperature, and any combinations thereof.

18. A non-transitory computer-readable storage medium storing computer-executable instructions that, when being executed by a processor of a user terminal, cause the user terminal to:
provide a first widget and a second widget on a user interface of the user terminal, wherein the first widget is associated with control of a first device in communication with the user terminal, the second widget is associated with control of a second device in communication with the user terminal, and the first device and the second device are configured to perform respective predefined acts sexually stimulating one or more human users;
activate joint control of the first device and the second device in response to a bundling operation used for bundling the first widget with the second widget; and
drive, in response to an operation used for triggering the joint control, the first device and the second device to perform the respective predefined acts synchronously,
wherein the computer-executable instructions further cause the user terminal to:
receive a dragging operation indicating one of the first and second widgets is dragged toward and close to another one of the first and second widget; and
provide a third widget on the user interface, wherein the third widget is associated with the joint control of the first device and the second device.

* * * * *